(12) United States Patent
Broadhurst, III

(10) Patent No.: US 7,910,620 B2
(45) Date of Patent: Mar. 22, 2011

(54) USES OF NEURAMINIDASE INHIBITORS IN INFECTIOUS DISEASES

(76) Inventor: Jack J. Broadhurst, III, Pinchurst, NC (US)

(*) Notice: Subject to any disclaimer, the term of this patent is extended or adjusted under 35 U.S.C. 154(b) by 177 days.

(21) Appl. No.: 11/112,138

(22) Filed: Apr. 22, 2005

(65) Prior Publication Data

US 2006/0241063 A1    Oct. 26, 2006

(51) Int. Cl.
- A01N 43/04 (2006.01)
- A01N 43/08 (2006.01)
- A61K 31/70 (2006.01)
- A61K 31/34 (2006.01)

(52) U.S. Cl. ............... 514/451; 514/43; 514/471

(58) Field of Classification Search ............ 514/451, 514/43, 471
See application file for complete search history.

(56) References Cited

U.S. PATENT DOCUMENTS

2004/0053858 A1* 3/2004 Berg ..................... 514/27
2004/0248825 A1* 12/2004 McCullers .............. 514/43

OTHER PUBLICATIONS

Elliott, Michael. "Zanamivir: from drug design to the clinic". Philosophical transactions of the Royal Society of London. Series B, Biological sciences. 2001. vol. 356. pp. 1885-1893.*
He et al. "Clinical Pharmacokinetics of the Prodrug Oseltamivir and its Active Metabolite Ro 64-0802". Clinical Pharmacokinetics. 1999. vol. 37, No. 6. pp. 471-484.*
McCullers et al. "Role of Neuraminidase in Lethal Synergism between Influenza Virus and Streptococcus pneumoniae". The Journal of Infectious Diseases. 2003. vol. 187. pp. 1000-1009.*
Young et al. "RWJ-270201 (BCX-1812): a novel neuraminidase inhibitor for influenza". Philosophical transactions of the Royal Society of London. Series B, Biological sciences. 2001. vol. 356. pp. 1905-1913.*
Nappert et al. "Determination of serum organic acids in puppies with naturally acquired parvoviral enteritis". The Canadian Journal of Veterinary Research. 2002. vol. 66. pp. 15-18.*
Stein, Expert Opinion on Investigational Drugs (2005) 14:107-109.*
Neill et. al., Expert Opinion on Investigational Drugs (2004) 13:1045-1063.*
Useh et. al., Veterinary Quarterly (2003) 25:155-159.*
Macintyre, D. (Feb. 2004, Management of Severe Parvoviral Enteritis. Presented at the Western Veterinary Conference, Las Vegas NV).*
Useh et. al. (Veterinary Quarterly (2003) 25:155-159).*
Elliot (Phil. Trans. R. Soc. Lond. B (2001) 356:1885-1893).*
Goodman and Gilman's The Pharmacological Basis of Therapeutics (Tenth Edition (2001), McGraw Hill, Chapter I, pp. 3-29).*

* cited by examiner

*Primary Examiner* — Brandon J Fetterolf
*Assistant Examiner* — Marcos Sznaidman
(74) *Attorney, Agent, or Firm* — Intellectual Property Law Group LLP; Juneko Jackson; Otto O. Lee

(57) ABSTRACT

The present invention relates to methods of decreasing the infectivity, morbidity and rate of mortality, in treating diseases associated with a variety of pathogenic organisms, specifically diseases involving one or more pathogens that require neuraminidase as a virulence factor. In addition, the present invention uses biology based therapy to treat neuraminidase dependent infections or diseases dependent on sialic acid metabolism.

18 Claims, No Drawings

USES OF NEURAMINIDASE INHIBITORS IN INFECTIOUS DISEASES

BACKGROUND

Many disease causing microorganisms, such as bacteria, fungi, and viruses, play a significant role in producing a myriad of diseases and conditions in humans and animals. Due to their widespread capability of pathogenic infectivity, morbidity and mortality, considerable activity has been devoted towards developing convenient effective methods to help prevent or treat these diseases caused by these pathogens.

For example, viruses such as influenza, have a high mortality rate in humans and are devastating to man and animals. It is estimated that more than $1 billion per year is lost in productivity from absence due to sickness from an influenza virus infection.

With respect to clinical veterinary medicine, there are many diseases, viral and bacterial, that are detrimental to animals. Viruses or bacteria that cause diseases that effect animals in the food industry, for example, cattle, pigs and chickens can be quite costly and result in billions of dollars lost in the food industry. These same microorganisms can wipe out large masses of domestic animals, such as cats and dogs, since they can be highly contagious and spread quickly, thus being detrimental to veterinary hospitals, kennels, and breeding facilities, resulting in both emotional and monetary loss. Recently, there have been several disease causing microorganisms that have jumped the species barrier, resulting in new variant diseases that are fatal to man.

Canine parvovirus (CPV), for example, has a high morbidity and mortality rate and is a life threatening infection that has been estimate to affect up to 1 million dogs per year in the United States. The disease resulting from parvovirus is typically almost always fatal, and there have been very few major advances in the way that dogs with canine parvovirus are treated. As a result, the disease is typically associated with a significant mortality rate. Most of the untreated dogs succumb to the diseases, and even with care, for example, in private practice, mortality rate still is quite high. In addition, the disease from a parvovirus infection is costly, both monetarily and emotionally for the dog's caretakers.

With canine parvovirus, the clinical disease is often characterized by fever, acute gastroenteritis, which can progress rapidly to shock and death. Septicemia and endotoxemia can play an important role in the pathogenesis of canine parvovirus. It has been found that when gnotobiotic (germ free) dogs were infected with canine parvovirus, they did not develop any signs of the illness. Similar findings were made with germ-free cats when exposed with highly pathogenic feline parvovirus. Thus, attempts have been directed to utilize treatments aimed at preventing or treating septicemia and endotoxemia. Unfortunately, these treatments have shown little or no benefit on survival of these animals.

Conventional methods towards the control of these disease causing microorganisms or pathogens, include vaccination, drug therapy and public health measures. Typically, one method of treatment of these types of diseases is antibiotic therapy, which has been found to be effective against diseases caused by bacteria. Although an invaluable advance, there are disadvantages of using antibiotic therapy, especially when strains of bacteria appear to be resistant to antibiotics.

Vaccines have also been used to treat diseases caused by viruses. However, there can be disadvantages involved with the production of suitable vaccines. First, the vaccines derived from whole killed or whole attenuated viruses, may retain residual disease causing activity. Further, vaccines typically are reformulated each year in response to antigenic variation and are known to be ineffective against new viral variants.

Additional disadvantages are that medications typically can be expensive, especially if animals are on antibiotics, for example, over a long course of time, eventually often resulting in an agonizing imminent death of these animals.

As those skilled in the art would appreciate, there is a need for methods that can decrease the infectivity, morbidity and mortality associated with exposures to such pathogens. Such compositions and methods of treatment should preferably not have the undesirable properties of promoting microbial resistance, or being toxic to the recipient. Still further, there is a need for treatment and prevention in diseases caused by microorganisms that are cost effective and do not take a long period of time. In addition, there is a need to provide treatment of infectious diseases by developing biology based therapies.

SUMMARY

The present invention is directed towards a method and treatment that meets these needs.

This invention provides a method of treating and preventing mucosal diseases, diseases associated with neuraminidase dependent bacteria and superinfections with a neuraminidase inhibitor.

In a preferred embodiment, the present invention uses biology based therapy to treat infectious diseases that have been previously treated with antibiotics or antivirals, alone or in combination, with limited success. Where there has been variable success in viruses with antiviral drugs, and antibiotics (conventional therapy), neuraminidase inhibitors according to the present invention have been proven to be successful and predictable. In a most preferred embodiment of the present invention, when neuraminidase inhibitors are used in these same diseases, the results have been dramatic.

Further, this invention relates to a means for reducing the severity of or preventing a neuraminidase dependent bacterial infection of the mucousal membrane tract following a viral infection by administering an effective amount of a neuraminidase inhibitor alone or in combination with a pharmaceutically acceptable compound prior to or during the course of the neuraminidase dependent bacterial infection, during the course of the superinfection or during the course of the coinfection.

In one embodiment, the present invention provides methods used for preventing disease or treating animals, including humans, exposed to pathogens or the threat of pathogens.

In still a further embodiment of the present invention, there is a method used for preventing animals, including humans, from getting a disease associated with the specific pathogen. For example, the animal is contacted with effective amounts of the compositions prior to exposure to pathogenic organisms. In other embodiments, the animal is contacted with effective amounts of the composition after exposure to pathogenic organisms. Thus, the present invention provides a method of both prevention and treatment of microbial infections.

In preferred embodiments, the present invention provides methods to decrease pathogenic organism infectivity, morbidity and mortality, by using an effective method of treatment where the composition comprises a compound that can include neuraminidase inhibitors.

In some preferred embodiments, the compound comprising a neuraminidase inhibitor is oseltamivir (TAMIFLU®, hereinafter referred to as TAMIFLU).

In another aspect of the present invention, the composition can include additional compounds, such as antibiotics, for example, which can be used in addition to the compound comprising the neuraminidase inhibitor.

In specific embodiments of the present invention, the method or treatment is performed for a sufficient amount of time to reduce the virulence factor of the pathogenic bacteria.

In a most preferred embodiment, the current invention provides a method of using neuraminidase inhibitors to treat: 1) infections involving neuraminidase dependent bacteria other than mucosal surfaces (blackleg, necrotic dermatitis), 2) one or more bacteria involving mucosal surfaces (colibacillosis or enteriopathic *E. coli* in all species, respiratory, renal, uterine, and mammary gland infections involving neuraminidase producing bacteria, *Salmonellosis* in all species, *Bordetella* and *Pasturella* respiratory infection in all species) and 3) superinfections that do involve mucosal surfaces (gastrointestinal, respiratory in all species).

In yet another preferred embodiment, the present invention provides a method of using an antiviral drug patented for human influenza to treat neuraminidase dependent bacterial infections, superinfections and coinfections which do not involve the human influenza virus A and/or B, for example, in clinical veterinary medicine.

In still another preferred embodiment, the present invention provides unexpected results of almost 100% effectiveness when used at 1 mg/lb every 12 hours for 10 treatments for therapeutic use and every 24 hours for 5 treatments for prophylactic use.

Finally, the present invention provides the use of a neuraminidase inhibitor to treat diseases involving neuraminidase dependent bacteria.

In the most preferred embodiment of the present invention, oseltamivir (Tamiflu) has been used to treat canine and feline parvoviral enteritis, canine kennel cough, feline upper respiratory infections, feline nephritis secondary to *E. coli*, and parvoviral enteritis in raccoons. Given the unique and universal role that sialic acid is known to play in infectious diseases involving neuraminidase dependent bacteria, the concept in the use of a neuraminidase inhibitor would be successful in treating all diseases involving these bacteria regardless of animal species is expected. Animal includes but is not limited to human beings, canine, feline, bovine, equine, avian, porcine and any other species known to those skilled in the art, for example, sheep goats and rabbits.

DESCRIPTION

According to the present invention, there is provided novel uses of selective neuraminidase inhibitors effective in shortening or stopping the pathophysiology of diseases involving one or more pathogens that require neuraminidase as a virulence factor.

Neuraminidase

Neuraminidases, (also known as sialidases) are known to those skilled in the art as enzymes that have been identified in many viruses, bacteria and eukaryotes that cleave sialic acid moieties and can be involved in many functions in vivo. It has been shown that neuraminidases can play a significant role in the pathogenesis of infectious diseases, whose etiologic agents produce neuraminidase to cleave sialic acids in infected tissues to facilitate their ability to invade a host. It has been shown that there is a positive correlation between the level of production of sialidases and the virulence of various bacterial strains. This virulence is further enhanced by different bacteria being able to produce more than one sialidase. Thus, many disease causing microorganisms possess a neuraminidase.

One example of a neuraminidase inhibitor that has been approved for the treatment of human influenza, is oseltamivir (TAMIFLU®, F. Hoffman-La Roche, Switzerland) and zanamivir (RELENZA®, Glaxo Wellcome, Inc., hereinafter referred to an RELENZA). Oseltamivir is a synthetic sialic acid analog that has been modified at the C4 position. Synthetic sialic acid analogs, such as oseltamivir have been demonstrated to inhibit the action of neuraminidases. Since their introduction in 1999, zanamivir and oseltamivir have been used successfully to treat human influenza A and B viral infections. In humans, neither zanamivir nor oseltamivir has been demonstrated to be effective in preventing serious influenza-related complications, such as bacterial or viral pneumonia or exacerbation of chronic diseases. Development of viral resistance to zanamivir and oseltamivir during treatment has been identified but does not appear to be frequent.

In some pathogens, including many enteric bacteria, neuraminidases typically are recognized as virulence factors. Neuraminidases cleave terminal sialic acid residues from cell surface molecules such as glycoproteins and glycolipids. As a result of this cleavage, internal sugar residues can be exposed that are normally protected and not available to pathogens. Neuraminidase activity can be particularly important for bacterial adhesion to mucosal surfaces. Mucous typically is highly sialylated and can be a major component of innate mucosal immunity. In mucosal diseases, commensal bacteria are separated from epithelial cells by a mucous barrier. Pathogenic bacteria have been shown to produce sialidases which can decrease the viscosity of the mucous and thus enable the bacteria to colonize on the epithelial cell membrane. Once in contact with the epithelial cell, a pathogen can become attached. With bacterial colonization and proliferation, there can be detachment and depletion of immunoglobin IgA. Bacterial endotoxins and exotoxins can be released resulting in local and distant tissue damage. Bacterial neuraminidases (sialidases) can cause the dissolution of the neuraminic acid located within the intercellular cement of the epithelial cells, allowing bacteria, their endotoxins, exotoxins and any environmental free sialic acid to enter the submucosa.

According to the present invention, it is known to those skilled in the art, the mechanism of hydrolyses of sialic acid compound during neuraminidase inhibition and pathogens that use sialic acid, is fully described and incorporated herein by reference in its entirety (Vrim et al., Microbiology and Molecular Biology Reviews, March 2004, p. 132-153).

A definitive role of neuraminidase activity in, for example, canine parvoviral infections, has not been established and it is thought that canine parvovirus does not have a neuraminidase in its genome. However, in one preferred embodiment of the present invention, it has been found that it is not essential for canine parvovirus to contain or utilize neuraminidases in order for them to enhance pathogenicity. Neuraminidases have been known to demonstrate enhanced pathogenicity in a synergistic fashion in several viral and bacterial superinfections involving mucosal surfaces. In some cases, for example, pneumococcal pneumonia secondary to influenza, viral neuraminidase activity enhanced the adhesion of the bacteria to the mucosal surface that resulted in increased bacterial invasion into tissues and resistant bacterial superinfection. Neuraminidases of bacterial origin alone are known as vitally important virulence factors.

The present invention provides the use of neuraminidase inhibitor to treat diseases involving neuraminidase dependent bacteria. Evidence to support this theory includes the following. It is known that the Fulani Pastoralists of rural Nigeria prevented blackleg infections in their cattle by feeding them the stem bark from two plants (*Tamarindus indicus* and *Com-*

*bretum fragrans*). These plants contained neuraminidase inhibitors in their stem bark. Blackleg is a lethal disease in cows caused by a neuraminidase dependent bacteria *Clostridium chauvoei*. In one preferred embodiment of the present invention, it has been demonstrated that bacteria must be present in the disease causing microorganism, for example, parvovirus infection, to result in significant pathology. Typically, germ free animals do not demonstrate any of the clinical disease that is seen in normal animals when they are challenged with virulent parvovirus strains. The pathology is thought to be attributed to septicemia and endotoxemia and is believed to originate from enteric bacteria. Several enteric bacterial species are known to have neuraminidase activity including *Escherichia coli, Campylobacterium, Salmonella, Shigella, Staphylococcus* and *Clostridium*. From the list, at least two of these species, *E. coli* and *Clostridium*, have been associated with morbidity and mortality in dogs with parvovirus.

In addition, germ-free kittens and germ-free puppies when exposed to pathogenic strains of feline and canine parvovirus, did not develop any clinical signs. It is known to those skilled in the art that the commensal microflora of puppies contains neuraminidase dependent bacteria (*Strep., E. coli, Staph., Clostridium, peptostreptococci, lactobacilli*). According to the present invention, it has been shown that *E. coli* and *Clostridium* have been associated with morbidity and mortality in dogs with parvovirus. In addition, neuraminidases have been demonstrated to enhance pathogenicity in a synergistic fashion in some viral and bacterial superinfections involving mucosal surfaces. Still further, the role of sialic acid metabolism in commensal and pathogenic strains of neuraminidase dependent bacteria provides support for the methods used in accordance with the present invention. Further evidence supporting the role of neuraminidases in infectious diseases includes knowing that the histopathological lesions associated with canine parvoviral enteritis were typical of those created by bacterial septicemia and endotoxemia.

In addition, most if not all of these commensal bacteria produce neuraminidase in order to provide sialic acid to use in their metabolic pathways. When canine parvovirus exits an infected gastrointestinal (GI) epithelial cell, sialic acid is released into the GI tract. The commensal bacteria begins to colonize and proliferate and produce their own neuraminidase. This excess neuraminidase can provide additional sialic acid and can also dissolve the neuraminic acid in intercellular cement providing a portal to submucosal tissue. In addition, neuraminidase can also displace epithelial cells' IgA.

Interleukin-8 is known as a cytokine produced by many cell types including endothelial cells, fibroblast, respiratory epithelial cells, macrophages and PMNs. With the release of IL-8, the PMNs can mobilize intracellular sialidases that move to their cell membrane and causes the release of sialic acid from the membrane surface. The removal of sialic acid residues from the PMN's cell membrane allows them to attach to the endotheial cell wall and move by diapedesis towards the tissues containing high levels of IL-8.

High levels of neuraminidase can also stimulate dendritic cells to interact with macraphages. Both CD4 and CD8 lymphocytes can also be stimulated to produce Th1 and Th2 cytokines.

Thus, in a preferred embodiment of the present invention, canine and feline parvoviral enteritis is shown to be a superinfection (requiring a virus+neuraminidase dependent bacteria living on a mucous substrate). The pathology seen at necropsy is solely due to endo and exotoxins produced by the commensal bacteria turned pathogenic. In a preferred embodiment of the present invention, parvoenteritis is not known as a viral disease, but that the pathobiology is due to excess neuraminidase. Thus, when a neuraminidase inhibitor like Tamiflu is administered early in the course of the disease or as a prophylactic, one can prevent the production of neuraminidase (sialidase) and one can prevent the commensal bacteria from becoming pathogenic. As used herein, "neuraminidase dependent bacteria" includes "neuraminidase producing bacteria."

In still yet another preferred embodiment of the present invention, the neuraminidase inhibitors can be used to target neuraminidase dependent bacterial infections, superinfections, and coinfections and not dependent on viral neuraminidase.

In one preferred embodiment of the present infection, "superinfection", as used herein, means that an infection requires both virus and bacteria combined together to produce pathology more severe than either can alone.

"Coinfection", as used herein, means two or more different bacterial strains together to produce pathology of a disease more severe than either can alone.

As used herein, the term "pathogen" refers to a microbe producing one or more virulence factors of which neuraminidase is one of. According to the present invention, the difference between pathogen and commensal bacteria is that commensal bacteria are not producing neuraminidase as virulence factors.

By the term "animal", as used herein, can be any animal species, including a human being, who is infected with, or is likely to be infected with, microorganism producing disease, which are believed to be pathogenic. Animal includes but is not limited to human beings, canine, feline, bovine, equine, avian, porcine and any other species known to those skilled in the art, for example, sheep goats and rabbits.

The inhibitors of interest in this invention are neuraminidase dependent bacteria inhibitors. Of particular interest are those which are specific for the neuraminidase enzyme. Since many commensal and pathogenic bacteria also used environmental (hosts) sialic acids as sources of carbon, nitrogen, energy and amino sugars for cell wall synthesis, microbial sialic acid metabolism has been established as a virulence determinant in a range of infectious diseases. Both commensal and pathogen bacteria have been known to modify their cell membranes with sialic acids in order to masquerade as "self" to avoid, obvert or inhibit host's innate immunity. Dehydration at the sialic acid reducing ends, leading to formation of a planar structure known as N-acetyl-2,3-didehydro-2-deoxyneuraminic acid (diddeoxyNeu5Ac [Neu5Ac2en]. The flattened Neu5Ac2en ring mimics the transition state during hydrolysis of sialoglycoconjugates (Sia-O-acceptors) by glycosylhydrolases designated sialidases (synonymous with neuraminidase). Neu5Ac2en is typically known as a sialidase or neuraminidase inhibitor. In particular, a preferred group of inhibitors are those neuraminidase inhibitors which are similar in structure to Neu5Ac2en. For example, Neu5Ac2en has been known to those skilled in the art, to serve as the lead compound for synthesis of one of the most well known sialidase inhibitor, zanamivir (Relenza). Most preferably, the neuraminidase inhibitors according to the present invention are those compounds that hydrolyze sialic acid.

Treatment

According to one embodiment of the present invention, an effective amount of compound, preferably a neuraminidase inhibitor can be administered to an animal. Typically, when a parvovirus infected animal presents symptoms such as vomiting/nausea and pain, traditional treatment involves administering fluids and cortisone for shock, antibiotics therapy and medicine for pain. In addition, anti-emetics can be administered to help alleviate nausea and vomiting.

The neuraminidase inhibitor can be administered in several ways: i) at the start of or during the course of the neuraminidase dependent bacterial infection, or some part thereof; or ii) at the start of or during the course of a superinfection infection or some part thereof; or iii) at the start of or during the course of a coinfection or some part thereof. In addition, the inhibitor can be administered prior to the onset of a neuraminidase dependent bacterial infection, superinfection or coinfection, and preferably continued for some period during the course of the bacterial infection, superinfection or coinfection. In a most preferred embodiment of the present invention, the neuraminidase inhibitor can be administered during the entire, or part of the length of a bacterial infection, a superinfection or a co-infection.

Most preferably, the neuraminidase inhibitor is administered within 48 hours of onset of first clinical signs.

By the term "an effective amount" is meant an amount of the compound in question which will in a majority of animals have either the effect that the disease caused by the pathogenic bacteria is cured or, if the substance has been given prophylactically, the effect that the disease is prevented from manifesting itself. The term "an effective amount" also implies that the substance is given in an amount which only causes mild or no adverse effects in the animal to whom it has been administered, or that the adverse effects may be tolerated from a medical and pharmaceutical point of view in the light of the severity of the disease for which the substance has been given.

For the purposes of this invention, it is preferred to administer an effective amount of the neuraminidase inhibitor in an amount from about 0.6 mg/lb to 12 mg/lb, more preferably 0.3 mg/lb to 10 mg/lb, and most preferably 1 mg/lb of the active ingredient. Too high a dose of neuraminidase inhibitor can be toxic. Too low of a dose may not be effective enough to treat or prevent the neuraminidase dependent disease.

The neuraminidase inhibitor can be administered by any route. The route of administration of the substance could be any conventional route of administration, i.e. oral, intravenous, intramuscular, intradermal, subcutaneous etc. A preferred formulation will be the oral route; oral immediate release tablet or an oral controlled release tablet. For treatment of a disease caused by a microorganism, the neuraminidase inhibitor can be administered up to 6 times per day, though twice or once a day dosing regime is preferred. More preferably, 10 doses over a period of 5 days. Most preferably, 6 doses over a period of 3 days or until the animal's health improves.

In yet another preferred embodiment of the present invention, for prevention of a disease caused by a microorganism, the neuraminidase inhibitor can be administered once a day for 5 days. Typically, with animals infected with parvovirus, administering the neuraminidase inhibitor with the first dose will stop the vomiting. After the $2^{nd}$ dose, the diarrhea will cease. By the $6^{th}$ dose, most clinical signs of the infection will have ceased.

In one preferred embodiment, a composition can be administered to an animal, the composition comprising a compound. The compound preferably is a selective neuraminidase inhibitor. More preferably, the compound is a neuraminidase inhibitor which is selective towards neuraminidase dependent bacteria. Preferably, the neuraminidase inhibitor can be selected from the group consisting of zanamivir (RELENZA®, Glaxo Wellcome, Inc), oseltamivir (TAMIFLU®, F. Hoffmann La Roche, Switzerland), rimantadine, rimantadine hydrochloride, amantadine, ribavirin and the like and any drug that are synthetic sialic acid analogs that can inhibit action of viral, bacterial and eukaryotic neuraminidases. Most preferably, the compound is a neuraminidase inhibitor that is oseltamivir. Oseltamivir (Tamiflu®) is available from Roche Pharma™ AG (Switzerland). Alternatively, oseltamivir can be prepared according to the methods described in U.S. Pat. No. 5,763,483 to Bischofberger et al and U.S. Pat. No. 5,866,601 to Lew et al., the disclosures of which are hereby incorporated by reference.

While the administration of neuraminidase inhibitor as the sole compound of the composition is most preferred, one or more of these neuraminidase inhibitors can be combined with other compounds for treating bacterial infections, superinfections and coinfections. For example, a neuraminidase inhibitor could be co-administered with a treatment during the course of the neuraminidase dependent bacterial infection. Examples of drugs that can also be used in combination with one or more other compounds without limitation, are antiinfective agents and/or other agents used to treat other acute or chronic ailments which include, antimicrobial compounds (such as antibiotics), antiviral compounds, anticancer compounds, vitamins, trace metal supplements, or ionic buffers designed to maintain or correct proper ionic balance in blood or other tissues, such drugs are alpha and beta interferon, Inosine pranobex, moroxydine hydrochloride and the like. If antibiotics are used, preferably, the antibiotic is selected from the group consisting of penicillins, benzylpenicillin, amoxycillin, ampicillin, cephalosporins, erythromycin and co-trimoxazole.

Appropriate dose ratio between a compound of the present invention and a second therapeutic compound for co-administration to an animal will be readily appreciated by those skilled in the art. Clearly, the combination therapies described herein are merely exemplary and are not meant to limit possibilities for other combination treatments or co-administration regimens.

EXAMPLES

The following examples show the importance of neuraminidase dependent bacteria in mucosal infections in several animal species.

TABLE 1

Neuraminidase Dependent Bacteria and Veterinary Diseases

| Bacteria spp: | Dog | Cat | Cow | Pig | Horse | Avian | Other |
|---|---|---|---|---|---|---|---|
| Actinobacillus | + | + | + | + | + | | |
| Actinomyces | + | + | + | + | + | + | + |
| Aeromonas | + | | + | + | | + | + |
| Bacteroides | + | + | + | + | + | | + |
| Bordetella | + | + | | + | + | + | + |
| Brucella | + | + | + | + | + | | + |
| Campylobacter | + | + | + | + | + | + | + |
| Clostridium | + | + | + | + | + | + | + |
| Corynebacterium | + | + | + | + | + | + | + |
| Enterobacter | + | + | + | + | + | | |
| E. coli | + | + | + | + | + | + | + |
| Erysipelothrix | + | + | + | + | + | + | + |
| Fusobacterium | + | + | + | + | + | + | |
| Klebsiella | + | + | + | + | + | | |
| Pasturella | + | + | + | + | + | + | + |
| Mannheimia | | | + | | | | + |
| Peptostreptococcus | + | + | + | + | + | + | |
| Proteus | + | + | + | + | + | + | + |
| Pseudomonas | + | + | + | + | + | + | + |
| Rhodococcus | | + | | | + | | |
| Salmonella | + | + | + | + | + | + | + |
| Serratia | + | + | + | + | + | + | + |
| Shigella | + | + | + | + | + | | + |
| Staphlococcus | + | + | + | + | + | + | + |
| Streptococcus | + | + | + | + | + | + | + |
| Vibrio | | | | | | + | + |
| Haemophilus | + | + | + | + | + | + | + |
| Arcanobacterium | + | + | + | + | | | + |

Neuraminidase dependent bacteria are those known to use sialiac acid (neuraminic acid) either as a source for carbon, nitrogen, energy and amino acids for cell wall synthesis. This microbial sialic acid metabolism is known to be a virulence factor in a number of infectious diseases. Tables (9-14) representing specific diseases in the various species are included.

TABLE 2

Superinfections in Veterinary Medicine

| Species: | Disease | Virus | Bacteria | Other |
|---|---|---|---|---|
| Canine | Parvoviral Enteritis | Canine Parvovirus CPV-2b > CPV-2a | Clostridium E. coli Streptococcus Staphylococcus | Salmonella Peptostreptococcus |
| | Tracheobronchitis (Kennel Cough) | Canine Adenovirus-1 Canine Adenovirus-2 Canine Parainfluenza | Bordetella bronchiseptica | Streptococcus Pasturella Pseudomonas Klebsiella E. coli |
| Feline | Parvoviral Enteritis (Panleukopenia) | Feline Parvovirus | Clostridium E. coli Streptococcus Staphylococcus Peptostreptococcus | |
| URI Complex | Feline Rhinotracheitis | Feline Herpesvirus-1 | Bordetella bronchiseptica | Streptococcus Pasturella Pseudomonas |
| | Feline Calicivirus | Feline Calicivirus | Bordetella bronchiseptica | Klebsiella E. coli Chlamydia |
| Bovine | Enzootic Pneumonia | Parainfluenza-3 (Pi-3) Bovine Respiratory Syncytial Virus (BRSV) Bovine Herpes-1 Reoviruses Rhinoviruses | Pasturella multocida Arcanobacterium pyognes Haemophilus somnus E. coli | Mycoplasma dispar Mycoplasma bovis Ureaplasma Chlamydia |
| | Shipping Fever or Pneumonic pasteurellosis | Pi-3 BRSV BHV-1 | Mannheimia haemolytica | Pasteurella multocida |
| | Infectious Bovine Rhinotracheitis (IBR) | Bovine Herpes-1 | Mannheimia haemolytica | Pasteurella multocida |
| | Bovine Viral Diarrhea | BVD-1 BVD-2 | Clostridium E. coli Streptococcus Staphylococcus Peptostreptococcus | |
| Porcine | Swine Influenza | Swine Influenza-A | Pasturella multocida | Arcanobacterium pyogenes Haemophilus |
| | Inclusion Body Rhinitis (Atrophic Rhinitis) Porcine Reproductive and Respiratory Syndrome (PRRS) | Porcine Cytomegalovirus (PCMV) PRRSV | Bordetella bronchiseptica Pasturella multocida Streptococcus suis Haemophilus parasuis Arcanobacterium suis E. coli | |
| | Transmissible Gastroenteritis (TGE) | TGEV | E. coli Clostridium | Streptococcus Staphlococcus |
| Equine | Equine Influenza | EIV-1 EIV-2 | Streptococcus zooepidermicis Staphlococcus aureus | |
| Avian | | | | |
| Chicken | Infectious Bronchitis | IBV | Respiratory E. coli | |
| Turkey | Hemorrhagic Enteritis | Adenovirus | Enteropathic E. coli Enteropathic E. coli | |
| | Poult Enteritis | Coronavirus | Enteropathic E. coli | |
| Ovine | Pneumonic Pasturellosis | ORSV Pi-3 Adenovirus Reovirus | Mannheimia haemolytica | Pasturella multocida |

Table 2 represents a partial list of infectious diseases in veterinary medicine known to be superinfections. Superinfections are those diseases requiring at least 2 different infectious microbes, that together produce a disease that neither are capable of doing alone. In these cases, one or more virus are associated with one or more neuraminidase dependent bacteria.

Feline Parvovirus and Upper Respiratory Complex and canine Parvoviral Enteritis and Tracheobronchitis have proven to be responsive to neuraminidase inhibitors. There is no reason, the other superinfections will not respond in the same manner.

TABLE 3

Parvo Cases at Chihuahua Kennel

| Case Number | Town State | Breed | Age | Parvo Test | IV Drugs | Tamiflu 1 mg/lb | Days to Recover |
|---|---|---|---|---|---|---|---|
| 1 | DC County Loving | Chihuahua | 6 wks | (+) | Yes | None | Died |
| 2 | Kennel, Purdon, TX | Chihuahua | 6 wks | No | Yes | None | Died |
| 3 | | Chihuahua | 6 wks | No | Yes | None | Died |
| 4 | | Chihuahua | 6 wks | No | Yes | None | Died |
| 5 | | Chihuahua | 6 wks | No | Yes | None | Died |
| 6 | | Chihuahua | 6 wks | No | Yes | None | Died |
| 7 | | Chihuahua | 6 wks | No | Yes | None | Died |
| 8 | | Chihuahua | 6 wks | No | Yes | None | Died |
| 9 | | Chihuahua | 6 wks | No | Yes | None | Died |
| 10 | Changed Veterinarian | Chihuahua | 6 wks | (+) | None | AM/PM | 5 |
| 11 | | Chihuahua | 6 wks | No | None | AM/PM | 3 |
| 12 | | Chihuahua | 6 wks | No | None | AM/PM | 3 |
| 13 | | Chihuahua | 6 wks | No | None | AM/PM | 3 |
| 14 | | Chihuahua | 6 wks | No | None | AM/PM | 3 |
| 15 | | Chihuahua | 6 wks | No | None | AM/PM | 3 |
| 16 | | Chihuahua | 6 wks | No | None | AM/PM | 3 |
| 17 | | Chihuahua | 6 wks | No | None | AM/PM | 3 |
| 18 | | Chihuahua | 6 wks | No | None | AM/PM | 3 |
| 19 | | Chihuahua | 6 wks | No | None | AM/PM | 3 |
| 20 | | Chihuahua | 6 wks | No | None | AM/PM | 3 |
| 21 | Exposed - Preventive | Chihuahua | 6 wks | No | None | AM | Healthy |
| 22 | | Chihuahua | 6 wks | No | None | AM | Healthy |
| 23 | | Chihuahua | 6 wks | No | None | AM | Healthy |
| 24 | | Chihuahua | Adult | No | None | AM | Healthy |
| 25 | | Chihuahua | Adult | No | None | AM | Healthy |
| 26 | | Chihuahua | Adult | No | None | AM | Healthy |
| 27 | | Chihuahua | Adult | No | None | AM | Healthy |
| 28 | | Chihuahua | Adult | No | None | AM | Healthy |

Table 3 represents 28 Chihuahua dogs and puppies that experienced an outbreak of canine parvoviral enteritis within their kennel. The initial treatment lasted one week and was consistent with traditional therapy. (IV fluids, antibiotics and antiemetics). During the first week, 9 puppies died and a second veterinarian was consulted.

The second veterinarian removed all IV treatment and started oral Tamiflu and AmoxiDrops on 11 puppies. This treatment was administered by the kennel staff with the veterinarian consulting by phone. All puppies survived with the new protocol.

The exposed dogs received 1 mg/lb of Tamiflu once a day for 5 days. Although exposed, these dogs remained healthy.

TABLE 4

Canine Parvo Cases at Sandcastle Kennels

| Case Number | Town State | Breed | Age | Parvo Test | IV Drugs | Tamiflu 1 mg/lb | Days to Recover |
|---|---|---|---|---|---|---|---|
| 1 | Foyil Oklahoma | Cocker | 6 wk | (+) | Yes | None | Died |
| 2 | | Cocker | 6 wk | No | Yes | None | Died |
| 3 | | Cocker | 6 wk | No | Yes | None | Died |
| 4 | | Cocker | 6 wk | No | Yes | None | Died |
| 5 | | Cocker | 6 wk | No | Yes | None | Died |
| 6 | | Cocker | 8 wk | (+) | Yes | None | Died |
| 7 | | Cocker | 8 wk | No | Yes | None | Died |
| 8 | | Cocker | 8 wk | No | Yes | None | Died |
| 9 | | Cocker | 8 wk | No | Yes | None | Died |
| 10 | Changed Veterinarian | Cocker | 6 wk | (+) | None | AM/PM | 3 |
| 11 | | Cocker | 6 wk | No | None | AM/PM | 5 |
| 12 | | Cocker | 8 wk | (+) | None | AM/PM | 3 |
| 13 | | Cocker | 8 wk | No | None | AM/PM | 5 |
| 14 | | Cocker | 8 wk | No | Yes | AM/PM | 5 |
| 15 | | Cocker | 10 wk | (+) | None | AM/PM | 3 |
| 16 | | Cocker | 11 wk | No | None | AM/PM | 3 |
| 17 | | Cocker | 12 wk | (+) | None | AM/PM | 4 |
| 18 | | Cocker | 12 wk | No | None | AM/PM | 5 |
| 19 | | Cocker | 12 wk | No | None | AM/PM | 3 |
| 20 | | Cocker | 12 wk | (+) | Yes | AM/PM | 4 |
| 21 | | Cocker | 14 wk | (+) | None | AM/PM | 5 |
| 22 | Exposed - Preventive | Cocker | 7 month | No | None | AM | Healthy |
| 23 | | Cocker | 7 month | No | None | AM | Healthy |
| 24 | | Cocker | 10 month | No | None | AM | Healthy |
| 25 | | Cocker | 10 month | No | None | AM | Healthy |

Table 4 represents of 25 cocker spaniel dogs and puppies that experienced an outbreak of canine parvoviral enteritis within their kennel. The initial treatment lasted one week and was consistent with traditional therapy consisting of IV fluids and antibiotics, antiemetics and steroids. During this period of time, 9 puppies died, and a second veterinarian was consulted.

The second veterinarian removed all IV treatment and oral Tamiflu and sulfadimethoxine/ormetoprim (antibiotic) were the only drugs administered to 11 of the puppies. The 12th puppy was taken to the veterinarian's clinic and received IV therapy. Those puppies remaining at the kennel were treated by the kennel staff.

The exposed dogs received 1 mg/lb of Tamiflu once a day for 5 days and did not develop canine parvoviral enteritis.

TABLE 5

Canine Parvoviral Enteritis Treated With Tamiflu

| Case Number | Town State | Breed | Age | Parvo Test | IV Drugs | Tamiflu 1 mg/lb | Days to Recover |
|---|---|---|---|---|---|---|---|
| 1-10 | Pinehurst, NC | Mix | 6-12 wks | (+) | None | AM/PM | 3 to 5 |
| 11 | Griffin, GA | Mix | 11 wks | (+) | None | AM/PM | 3 |
| 12 | | Mix | 14 wks | (+) | Yes | AM/PM | 2 |
| 13 | | Mix | 14 wks | (+) | Yes | AM/PM | 2 |
| 14 | Rockford, IL | GSH | 8 wks | (+) | Yes | AM/PM | 3 |
| 15 | Clayton, NC | JRT | 7 months | (+) | Yes | AM/PM | 5 |
| 16 | Carthage, NC | Mix | 19 wks | (+) | None | AM/PM | 3 |
| 17 | | Mix | 20 wks | (+) | None | AM/PM | 4 |
| 18 | Apple Valley, CA | Beagle | Pup | (+) | Yes | AM/PM | 3 |
| 19 | Millington, TN | GSH | Pup | (+) | Yes | AM/PM | 2 |
| 20 | Douglas, GA | Basset | 12 wks | (+) | Yes | AM/PM | 2 |
| 21 | | It. Greyh. | 12 wks | (+) | Yes | AM/PM | 3 |
| 22 | | Boxer | 12 wks | (+) | Yes | AM/PM | 3 |
| 23 | Canton, OH | Rotti-x | 6 months | (+) | Yes | AM/PM | 2 |
| 24 | Griffin, GA | Mix | Pup | (+) | Yes | AM/PM | 3 |
| 25 | | Mix | Pup | (+) | Yes | AM/PM | 3 |
| 26 | | Mix | Pup | (+) | Yes | AM/PM | 2 |
| 27 | Salisbury, MD | Pit Bull-x | 6 wks | (+) | None | AM/PM | 2 |
| 28 | Redford, MI | Pit Bull | 9 months | Corona | Yes | AM/PM | 4 |
| 29 | Grand Rapids, MI | Mix | Pup | (+) | Yes | AM/PM | 3 |
| 30 | | Mix | Pup | (+) | Yes | AM/PM | 3 |
| 31 | | Mix | Pup | (+) | Yes | AM/PM | 3 |
| 32 | Bend, OR | Bost. Terr. | 6 months | (+) | Yes | AM/PM | 2 |
| 33 | Mishawaka, IN | Eng. Sett. | 14 wks | None | Yes | AM/PM | 4 |
| 34 | Vancouver, WA | Rotti | 8 wks | (+) | Yes | AM/PM | 5 |
| 35 | Atlanta, GA | Mix | 7 wks | (+) | Yes | AM/PM | 3 |
| 36 | Jonesboro, AR | Min. Sch. | 6 months | (+) | Yes | AM/PM | 2 |
| 37 | | Beagle-x | 5 months | (+) | Yes | AM/PM | 4 |
| 38 | Columbia, MO | Mix | Pup | (+) | Yes | AM/PM | 3 |
| 39 | Ocoee, FL | Shar Pei | 4 months | (+) | None | AM/PM | 2 |
| 40 | Mishawaka, IN | Mix | 14 wks | (weak) | Yes | AM/PM | 4 |
| 41 | | Mix | 4 months | (+) | Yes | AM/PM | 3 |
| 42 | | Mix | 12 wks | (+) | Yes | AM/PM | 3 |
| 43 | Atlanta, GA | Mix | 10 wks | (+) | None | AM/PM | 3 |
| 44 | | Gold. Ret. | 8 wks | (+) | Yes | AM/PM | 2 |
| 45 | Los Angeles, CA | St. Ber.mix | 10 wks | (+) | None | AM/PM | 2 |
| 46-48 | Garden City, KS | Lab | 6 months | (+) | None | AM/PM | 3 |
| | (exposed) | B. CollieX | 12 weeks | (weak) | None | AM/PM | Normal |
| | | B. CollieX | 12 weeks | (+) | None | AM/PM | 4 |

States 15
DVMS 20
Puppies 48

Summary:

Table 5 represents 48 individual cases of Canine Parvoviral Enteritis treated with 1 mg/lb Tamiflu AM/PM for 10 treatments. Cases posted VIN's Infectious Dz Board by 20 veterinarians practicing in 15 states.

TABLE 6

Feline Parvoenteritis Treated with Tamiflu

| Case Number | Town State | Breed | AgeSex | Parvo Test | IV Drugs | Tamiflu 1 mg/lb | Days to Recover |
|---|---|---|---|---|---|---|---|
| 1 | Smithfield, NC | Siamese | 5 M/m | (+) | Yes | AM/PM | 2 |
| 2 | | Siamese | 5 M/fem | (+) | Yes | AM/PM | 3 |
| 3 | Alberta, Canada | DSH | 14 wk/m | no WBCs | Yes | AM/PM | 3 |

TABLE 6-continued

Feline Parvoenteritis Treated with Tamiflu

| Case Number | Town State | Breed | AgeSex | Parvo Test | IV Drugs | Tamiflu 1 mg/lb | Days to Recover |
|---|---|---|---|---|---|---|---|
| 4 | (Exposed) | DSH | 20 wk/fem | condomate | None | AM | Normal |
| 5 | Phoenix, AZ | DSH | 10 wk/fem | (+) | SQ fluids | AM/PM | 4 |
| 6 | | DSH | 10 wk/fem | (+) | SQ fluids | AM/PM | 4 |

Table 6 represents 5 cases of Feline Parvoviral Enteritis with Tamiflu at 1 mg/lb AM/PM for 10 treatments. One kitten exposed, remained normal when given Tamiflu at 1 mg/lb once a day for 5 days.

TABLE 7

Raccoon Parvoenteritis/Distemper Treated with Tamiflu

| Case Number | Town State | Breed | Age | Parvo Test | IV Drugs | Tamiflu 1 mg/lb | Days to Recover |
|---|---|---|---|---|---|---|---|
| 1 | Hudson, IL | Raccoon | Adult/Male | none | none | AM/PM | 3 |
| 2 | | Raccoon | Adult/Fem | none | none | AM/PM | 3 |
| 3 | Chiefland, FL | Raccoon | Adult | none | none | AM/PM | 3 |
| 4 | | Raccoon | Adult | none | none | AM/PM | 3 |
| 5 | | Raccoon | Adult | none | none | AM/PM | 3 |

Table 7 represents 5 raccoons treated with Tamiflu at 1 mg/lb given every 12 hrs for 10 treatments. Treatment administered by civilian rehabbers at their homes. Granules mixed with pancake syrup.

Raccoons represent the 5th species (cow, dog, cat, mice) in which a neuraminidase inhibitor has been successful in treating or preventing a disease associated with neuramimidase dependent bacteria. Before using Tamiflu, the hemorrhagic gastroenteritis (Parvo) in raccoon was 100% fatal. While the numbers are small they are significant as they prove the pathobiology seen in hemorrhagic gastroenteritis of raccoon is neuraminidase driven. Treatment was administered by untrained lay personnel at the rehab centers.

TABLE 8

Canine Kennel Cough Cases Treated With Tamiflu

| Case Number | Town State | Breed | Age | Oral Antibiotic | Cough Suppressant | Tamiflu AM/PM | Days to Recover |
|---|---|---|---|---|---|---|---|
| | Holding Kennels for Pet Stores | | | | | 1 mg/lb | |
| 11-175 | Lynbrook, NY | Mixed | 8-12 wks | Doxy | None | AM/PM | 3-5 days |
| 1-65 | New Hyde Park, NY | Mixed | 8-12 wks | Doxy | None | AM/PM | 3-5 days |
| 1-60 | Lawrence, NY | Mixed | 8-12 wks | Doxy | None | AM/PM | 3-5 days |
| | Racing Greyhounds at Race Tracks | | | | | 1 mg/lb | |
| 1, 2, 3 | Miami, Florida | Greyhound | 1.5-4 yr. | None | None | AM/PM | 3-5 days |
| 1-46 | Group A | Greyhound | 1.5-4 yr. | Doxy | Dextromet | none | No Change |
| 1-46 | Group B | Greyhound | 1.5-4 yr. | Cephalexin | Torbutrol | none | No Change |
| 1-47 | Group C | Greyhound | 1.5-4 yr. | Clamamox | Hycodan | none | No Change |
| ***After 5 days, DVM stopped antibiotics and cough suppressants and started Tamiflu | | | | | | | |
| 1-46 | Group A | Greyhound | 1.5-4 yr. | None | None | AM/PM | 3-5 days |
| 1-46 | Group B | Greyhound | 1.5-4 yr. | None | None | AM/PM | 3-5 days |
| 1-47 | Group C | Greyhound | 1.5-4 yr. | None | None | AM/PM | 3-5 days |
| 1-70 | Kan. City, Kansas | Greyhound | 1.5-4 yr. | Doxy | None | AM/PM | 3-5 days |
| ***Track Veterinarian had to use 0.5 mg/lb due to cost | | | | | | 0.5 mg/lb | |
| 1-72 | Mobile, Alabama | Greyhound | 1.5-4 yr. | Pen - G | None | (+) | 5-10 days |

Infectious Canine Tracheobronchitis (ICT) or Kennel Cough is a highly infectious superinfection spread by aerosol droplets. The 3 holding kennels represent the first attempt at a herd health plan. The sick dogs were given Tamiflu at 1 mg/lb AM/PM for 5 days. They recovered in 3-5 days. Those not showing clinical signs and any new puppy entering the kennel were given 1 mg/lb once a day for 5 days. This program reduced illness to below 5 percent, and cost of veterinary care by over 75%.

Kennel Cough outbreaks at Greyhound racing tracks result in the tracks being closed. In Miami, a total of 142 dogs became infected with ICT. They were separated into 4 groups: Group A,B and C received a different combination of antibiotic/cough suppressant. Three dogs were given Tamiflu at 1 mg/lb AM/PM for 10 treatments. Groups A,B and C's clinical course was unchanged after 5 days of conventional therapy. Started Tamiflu, and dogs recovered in 3-5 days.

The Miami experiment was the basis for treatment during a similar ICT outbreak at a Kansas City track.

Cost of Tamiflu was a factor during an ITC outbreak in Mobil, Ala. They The DVM decided to give half the recommended dose (0.5 mg/lb). The results were better than conventional, but longer than when the recommended dose is used. This trial demonstrates that the response is dose related.

TABLE 9

Neuraminidase Dependent Bacteria and *Canine* Diseases

| Bacteria spp: | Respiratory | Urogenital | Gastrointestinal | Other |
|---|---|---|---|---|
| *Actinomyces* | Pyothorax Peritonitis | | | Deep Wounds |
| *Aeromonas* | | | | Septicemia |
| *Bacteroides* | | | | Bone Infect. |
| *Bordetella* | Kennel Cough Distemper Upper Resp. Infect. | | | |
| *Brucella* | | Abortion Infertility | | |
| *Campylobacter* | | | Gastroenteritis | |
| *Clostridium* | | | Gastroenteritis Parvoenteritis | Tetnus Botulism |
| *Corynebacterium* | | | | |
| *Enterobacter* | | | | |
| *E. coli* | Upper Respiratory Pneumonia | Pyometra Mastitis Renal Infections Cystitis | Colibacillosis Parvoenteritis | |
| *Erysipelothrix* | | | | Endocarditis |
| *Fusobacterium* | | | | |
| *Klebsiella* | Upper Respiratory Pneumonia | Cystitis | | |
| *Pasturella* | Upper Respiratory Pneumonia | | | |
| *Peptostreptococcus* | | | | Abscesses |
| *Proteus* | | Upper and Lower Urinary Tract | Gastroenteritis | Otitis |
| *Pseudomonas* | Upper Respiratory Pneumonia | Pyometra Cystitis | | Otitis Dermatitis |
| *Rhodococcus* | | | | |
| *Salmonella* | | | Gastroenteritis | |
| *Serratia* | | | | |
| *Shigella* | | | Gastroenteritis | |
| *Staphlococci* | Upper Respiratory Pneumonia | Pyometra Mastitis Cystitis | | Otitis Dermatitis |
| *Streptococci* | Pneumonia | Pyometra Mastitis Cystitis | Parvoenteritis | Septicemia Puppy Strangles |
| *Haemophilus* | | | | |
| *Arcanobacterium* | | | | |

Table 9 is a partial listing of known neuraminidase dependent bacteria and the infectious diseases associated with them in the dog.

TABLE 10

Neuraminidase Dependent Bacteria and *Feline* Diseases

| Bacteria spp: | Respiratory | Urogenital | Gastrointestinal | Other |
|---|---|---|---|---|
| *Actinomyces* | Pyothorax Peritonitis | | | Abscess |
| *Aeromonas* | | | | |
| *Bacteroides* | Emphyema | | | Abscess |

TABLE 10-continued

Neuraminidase Dependent Bacteria and *Feline* Diseases

| Bacteria spp: | Respiratory | Urogenital | Gastrointestinal | Other |
|---|---|---|---|---|
| *Bordetella* | Upper Respiratory Pneumonia | | | |
| *Brucella* | | | | |
| *Campylobacter* | | | Gastroenteritis | |
| *Clostridium* | | | Gastroenteritis Panleukopenia | Tetnus |
| Corynebacterium | | | | |
| Enterobacter | | | | |
| *E. coli* | | Pyometra Mastitis Renal Infections Cystitis | Colibacillosis Panleukopenia | |
| *Erysipelothrix* | | | | |
| *Fusobacterium* | | | | |
| *Klebsiella* | Upper Respiratory Pneumonia | Cystitis | | |
| *Pasturella* | Upper Respiratory Pneumonia | | | |
| *Peptostreptococcus* | | | | |
| *Proteus* | | | | Otitis |
| *Pseudomonas* | Upper Respiratory Pneumonia | Pyometra Cystitis | | Otitis Abscess |
| *Rhodococcus* | Pyothorax | | | Abscess |
| *Salmonella* | | | Gastroenteritis | |
| *Serratia* | | | | |
| *Shigella* | | | Gastroenteritis | |
| *Staphlococci* | Upper Respiratory Pneumonia | Pyometra Mastitis Cystitis | | Otitis Dermatitis |
| *Streptococci* | Pneumonia | Pyometra Mastitis Cystitis | Panleukopenia | Septicemia |
| *Haemophilus* | | | | |
| *Arcanobacterium* | | | | |

Table 10 is a partial listing of known neuraminidase dependent bacteria and the infectious diseases associated with them in the cat.

TABLE 11

Neuraminidase Dependent Bacteria and *Bovine* Diseases

| Bacteria spp: | Respiratory | Urogenital | Gastrointestinal | Other |
|---|---|---|---|---|
| *Actinomyces* | Pneumonia | Mastitis Endometritis Umbilical Infections Seminal Vesiculitis | | "Lumpy Jaw" Arthritis Endocarditis Abscess |
| *Aeromonas* | | Mastitis | | |
| *Bacteroides* | | Mastitis | Gastroenteritis | Foot Rot Osteomyelitis |
| *Brucella* | | Abortion Orchitis | | |
| *Campylobacter* | | Epizootic Infertility Embryonic Death Abortion | | |
| *Clostridium* | | Gangrenous Mastitis | Enterotoxaemia Maligant Edema Gas Bacillary Haemoglobinuria | Tetanus Botulism Blackleg Gangrene |
| *Corynebacterium* | | Pyelonephritis Cystitis Mastitis | | |
| *Enterobacter* | | Coliform Mastitis | | |
| *E. coli* | | Mastitis | "White Scours" Colibacillosis | Septicemia Joint III |
| *Fusobacterium* | Calf Diphtheria | Mastitis Metritis | Liver Abscess in Feedlot Hepatic Necrobacillosis | |
| *Klebsiella* | | Mastitis | | |

TABLE 11-continued

Neuraminidase Dependent Bacteria and *Bovine* Diseases

| Bacteria spp: | Respiratory | Urogenital | Gastrointestinal | Other |
|---|---|---|---|---|
| *Pasturella* | "Shipping Fever" "Enzootic Pneumonia" | | | Hemorrhagic Septicemia Fibrogranulomatous Disease |
| *Peptostreptococcus* | | Summer Mastitis | | |
| *Proteus* | | | Enteritis | |
| *Pseudomonas* | Focal Pneumonia | Mastitis Uterine Infections | Enteritis | Dermatitis Abscess Arthritis |
| *Salmonella* | | Abortion | Enteritis | Septicaemia Meningitis Joint III |
| *Serratia* | | Mastitis | | Dry Gangrene in Calves |
| *Staphlococci* | | Mastitis Udder impetigo | | |
| *Streptococci* | | Mastitis/Metritis | | |
| *Haemophilus* | Pneumonia | | | |
| *Arcanobacterium* | Pneumonia | Mastitis | Liver Abscess | Foot Rot |

Table 11 is a partial listing of known neuraminidase dependent bacteria and the infectious diseases associated with them in the cow.

TABLE 12

Neuraminidase Dependent Bacteria and *Porcine* Diseases

| Bacteria spp: | Respiratory | Urogenital | Gastrointestinal | Other |
|---|---|---|---|---|
| *Actinomyces* | Pneumonia | Pyogranulomatous Mastitis Endometritis Umbilical Infections Seminal Vesiculitis | | Arthritis Lymphadenitis |
| *Aeromonas* | | | Diarrhea | |
| *Bacteroides* | | | Diarrhea in Piglets | Abscess |
| *Bordetella* | Atrophic Rhinitis Bronchopneumonia in Young Piglets | | | |
| *Brucella* | | Abortion Orchitis Infertility | | Arthritis Spondylitis |
| *Campylobacter* | | Intestinal Adenomatosis | Diarrhea | |
| *Clostridium* | | | | Tetnus Botulinum Black Leg Maligant Edema Hemorrhagic Enterotoxemia |
| *Corynebacterium* | | Pyelonephritis | | |
| *Enterobacter* | | Mastitis-Metritis Agalactia Complex(MMA) | | |
| *E. coli* | Associated with PRRSV | Mastitis Mastitis-Metritis Agalactia Complex(MMA) | Neonatal Diarrhea Colisepticemia Weaning Enteritis | Piglet Meningitis Sudden Edema/death |
| *Erysipelothrix* | | Acute Abortion | | "Diamond Skin Disease" Vegetative Endocarditis Polyarthritis |
| *Fusobacterium* | "Bull-Nose" | | Necrotic Enteritis | Liver Abscess |
| *Pasturella* | Pneumonia Assoc. w/PRRSV Atrophic Rhinitis | | | |
| *Peptostreptococcus* | | | | |
| *Pseudomonas* | Respiratory Infections | Abortion | Enteritis | Otitis Arthritis |
| *Rhodococcus* | | | Cervical Lymphadenitis | |
| 1 *Salmonella* | | | Hog Cholera Chronic Enteritis | Septicemia |
| *Serpulina* | | | Swine Dysentery | |
| *Staphlococci* | | Mastitis Endometritis Udder Impetigo | | Exudative Epidermitis or Greasy Pig Disease |

TABLE 12-continued

Neuraminidase Dependent Bacteria and *Porcine* Diseases

| Bacteria spp: | Respiratory | Urogenital | Gastrointestinal | Other |
|---|---|---|---|---|
| *Streptococci* | | Rhinitis, Pneumonia | | Lymphadenitis |
| | | assoc. w/Porcine Reproductive and Respiratory Syndrome | | Arthritis |
| *Haemophilus influenzae* | Porcine Reproductive and Respiratory Syndrome | | | |
| *Arcanobacterium* | Pneumonia | | | |

Table 12 is a partial listing of known neuraminidase dependent bacteria and the infectious diseases associated with them in the pig.

TABLE 13

Neuraminidase Dependent Bacteria and *Equine* Diseases

| Bacteria spp: | Respiratory | Urogenital | Gastrointestinal | Other |
|---|---|---|---|---|
| *Actinomyces* | | | | Poll Evil |
| | | | Fistulous Withers | |
| *Aeromonas* | | | | |
| *Bacteroides* | | | Diarrhea in Foals | Osteomylitis |
| | | | Buccal Cavity Lesions | |
| *Bordetella* | Respiratory Infections | | | |
| *Brucella* | | | | Poll Evil |
| | | | Fistulous Withers | |
| *Campylobacter* | | | | |
| *Clostridium* | | | Enteritis | Tetanus |
| | | | | Botulism |
| *Corynebacterium* | | | Ulcerative Lymphangitis | |
| *Enterobacter* | | Metritis | | |
| *E. coli* | | | Enteritis | |
| *Erysipelothrix* | | | | |
| *Fusobacterium* | | | "Thrush" involving the frog | |
| *Klebsiella* | Pneumonia in Foals | Metritis | | Abscess |
| | | Cervicitis | | |
| *Pasturella* | Respiratory Infections | | | |
| | Pneumonia | | | |
| *Peptostreptococcus* | | | | |
| *Proteus* | | Kidney infections | | |
| | | Cystitis | | |
| *Pseudomonas* | Lung Abscesses | Metritis | | Eye Infections |
| | Glanders | | | Lymphangitis with ulcers |
| | | | | along lymphatics(Farcy) |
| *Rhodococcus* | Bronchopneumonia | | | |
| *Salmonella* | | Abortion | Sever Enteritis | Septicemia |
| *Serratia* | | | | |
| *Shigella* | | | | |
| *Staphlococci* | | Mastitis | | |
| | | Botryomycosis after | | |
| | | Castration | | |
| *Streptococci* | Pneumonia | Endometritis | | Foal Lymphangitis |
| | | Mastitis | | Abscess |
| | | Abortion | | Strangles |
| | | Navel Infections | | Purpura Hemorrhagica |
| | | Genital Infections | | |
| *Haemophilus* | | | | |
| *Arcanobacterium* | | | | |

Table 13 is a partial listing of known neuraminidase dependent bacteria and the infectious diseases associated with them in the horse.

TABLE 14

Neuraminidase Dependent Bacteria and *Avian* Diseases

| Bacteria spp: | Respiratory | Urogenital | Gastrointestinal | Other |
|---|---|---|---|---|
| *Actinobacillus* | | | | |
| *Actinomyese* | | | | |
| *Aeromonas* | | | | Septicemia |
| *Bacteroides* | | | | |
| *Bordetella* | Turkey Coryza | | | |

TABLE 14-continued

| Neuraminidase Dependent Bacteria and *Avian* Diseases | | | | |
|---|---|---|---|---|
| Bacteria spp: | Respiratory | Urogenital | Gastrointestinal | Other |
| | Rhinotracheitis | | | |
| | Sinusitis | | | |
| *Campylobacter* | | | Avian Vibrionic Hepatitis | |
| *Clostridium* | | | Necrotic Enteritis | Tetanus |
| | | | Ulcerative Enteritis | Botulism |
| | | | Necrotic Dermatitis | |
| | | | | "Struck" |
| *Corynebacterium* | | | | |
| *Enterobacter* | | | | |
| *E. coli* | Airsacculitis | Ovarian Infection | Peritonitis | Omphalitis |
| | Infectious Bronchitis | | Hemorrhagic Enteritis | |
| | | | Turkey Poult Enteritis | |
| | | | Colibacillosis | |
| | | | Coligranuloma in liver and intestines | |
| *Erysipelothrix* | | | | Spleenitis |
| | | | Endocarditis | |
| | | | | Arthritis |
| *Fusobacterium* | Avian Diphtheria secondary to Fowl Pox | | | |
| *Klebsiella* | | | | |
| *Pasturella* | Fowl Plague | | Fowl Cholera | Fibrinous |
| | Pasteurellosis | | | Polyserositis |
| *Peptostreptococcus* | | | | |
| *Proteus* | | | | |
| *Pseudomonas* | | | | |
| *Rhodococcus* | | | | |
| *Salmonella* | | | Pullorum Disease | Fowl |
| | | | White Diarrhea | Typhoid |
| | | | | Paratyphoid |
| *Serratia* | | | | Septicemia |
| *Staphlococci* | | | Bumble-Foot | |
| | | | | Arthritis |
| | | | | Breast Blister |
| *Streptococci* | | | | Septisemia |
| | | | | Endocarditis |
| *Vibrio* | | | Cholera-like Enteric Disease | |
| *Haemophilus* | Infectious Coryza | | | |
| *Arcanobacterium* | | | | |

Table 14 is a partial listing of known neuraminidase dependent bacteria and the infectious diseases associated with them in chickens, turkeys, ducks.

TABLE 15

| Neuraminidase Dependent Bacteria and Other Species' Diseases Sheep, Goats and Rabbits | | | | |
|---|---|---|---|---|
| Bacteria spp: | Respiratory | Urogenital | Gastrointestinal | Other |
| *Actinomyces* | | | | |
| *Aeromonas* | | | | |
| *Bacteroides* | | | Contagious Foot Rot | |
| | | | Enterotoxic Diarrhea | |
| *Bordetella* | "Snuffles" in Rabbits | | | |
| | Bronchopneumonia | | | Septicemia |
| *Brucella* | | Abortion | | |
| | | Epididymitis | | |
| *Campylobacter* | | Abortion | | |
| | | Ovine Genital Campylobacteriosis | | |
| *Clostridium* | | Pulpy Kidney Disease | Enterotoxemia | Tetanus |
| | | Gangrenous Mastitis | Mucoid Enteritis/Rabbits | Botulism |
| | | | Maligant Edema | |
| | | | Braxy | Big Head |
| | | | Hemorrhagic Enterotoxemia | |
| | | | Struck | |
| *Corynebacterium* | | | Caseous Lymphadenitis | |
| *Enterobacter* | | | | |
| *E. coli* | | Mastitis | Colibacillosis | |
| | | | Colisepticemia | |
| | | | "Watery Mouth" in Nenatal Lambs | |
| *Erysipelothrix* | | | | Septicemia |
| | | | | Arthritis |

TABLE 15-continued

Neuraminidase Dependent Bacteria and Other Species' Diseases
Sheep, Goats and Rabbits

| Bacteria spp: | Respiratory | Urogenital | Gastrointestinal | Other |
|---|---|---|---|---|
| *Fusobacterium* | | | | Endocarditis Foot Abscess Necrobacillosis of lips and mouth |
| *Klebsiella* | | | | |
| *Pasturella* | Pleuropneumonia | Mastitis | | Septicemia |
| *Peptostreptococcus* | | | | |
| *Proteus* | | | Diarrhea in Goats. Lambs | |
| *Pseudomonas* | | | | Arthritis Lymphangitis |
| *Rhodococcus* | | | | |
| *Salmonella* | | Abortion in Ewes | Enteritis | Septicemia |
| *Serratia* | | | | |
| *Shigella* | | | | |
| *Staphlococci* | | Mastitis | | Dermatitis Abscess Periorbital Eczema Conjunctivitis |
| *Streptococci* | Pneumonia | Chronic Mastitis | | Arthritis Pericarditis |
| *Haemophilus* | | | | |
| *Arcanobacterium* | | Mastitis | | Foot Abscess |

Table 15 is a partial listing of known neuraminidase dependent bacteria and the infectious diseases associated in sheep, goats, rabbits.

TABLE 16

Clinical Trial: Tamiflu and *E. coli*

| Veterinarian or Clinic: | | Cat Health Clinic | | | Phone: | (910) 295-2287 | |
|---|---|---|---|---|---|---|---|
| | Address: | 2212 Midland Road Street | | Pinehurst City | | NC State | 28374 Zip |
| Patient: | Owner: | Vince and Peggy Meads | | | | | |
| | Name: | Pinga | Age: Sex: | Oct. 19, 1998 FS | | Breed: | Siamese |

Medical History:
  Presented Nov. 22, 2004 for vomiting beginning on Nov. 19, 2004. Blood for CBC/Chem Profile submitted along with urine for culture sensitivity. Started Zeniquin at 12.5 mg/day dissolved in Rebound electrolyte solution. Reglan was given for nausea.
  When seen on Nov. 24, 2004, was presented on a blanket in lateral recumbancy. Had urinated blood tinged urine on bedding. Lab reported isolating *E. coli*, sensitivity pending. Other abnormal values: BUN (55 mg/dl), Phos (10.6 mg/dl), Sodium (162 mEq/L), Osm (340 mOs/L and WBC elevated at 19,100. Since Pinga had gotten progressively worse over the course of antibiotic therapy, and now appeared to be approaching endotoxic shock Tamiflu was begun at 2 PM. *E. coli* is a neuraminidase dependent bacteria.

Physical Exam:         Temp: 99.9 F.     Pulse: 140/min     Weight: 8.06 lbs.
                       Resp:             % Dehy: Slight     Parvo Test: Not Done
                Pinga was presented laying on her side unable to sit or stand.
                She had a decreased capillary refilling time and temperature was subnormal.
         Tamiflu dose: 1 mg/lb . . . that dose given every 12 hours for a total of 10 treatments

| Treatment | Drugs/Fluids | Observations |
|---|---|---|
| 1st. | | |
| Date: Nov. 24, 2004 Temp: 99.8 F. | Dissolved 12.5 mg Zeiniquin in 12 cc of Rebound and gave PO Gave 12 mg Tamiflu (1 cc)/PO at 2:00 PM | Can not sit or stand, urinated in bed this morning . . . urine was blood tinged. *E. coli* cultured . . . sensitvity pending. |
| 2nd. | | |
| Date: Nov. 24, 2004 | Gave 12 mg Tamiflu (1 cc) at 5:35 PM | Pinga is more alert and has not vomited since receiving Tamiflu. Can not stand, but can sit upright. |
| 3rd. | | |
| Date: Nov. 25, 2004 Temp: 99.5 F. | Dissolved 12.5 mg Zeniquin in 12 cc of Rebound and gave PO Gave 12 mg Tamiflu/PO at 10:15 AM Tamiflu and Parvo Clinical Trial | No vomiting since starting Tamiflu . . . is drinking water . . . walked 20 feet and urinated a clear yellow colored urine next to litter box. About 1:30 AM, left bed, walked to owne's bed, jumped up and began to purr |

TABLE 16-continued

Clinical Trial: Tamiflu and *E. coli*

4th.

| Date:<br>Nov. 25, 2004<br>Temp:<br>98.9 F. | Gave 12 mg Tamiflu/PO at 5:30 PM | Urinated, was normal yellow color . . . has begun to walk around house . . . jumped and ran when attempted to brush . . . Pinga is more alert in clinic |
|---|---|---|

5th.

| Date:<br>Nov. 26, 2004<br>Temp:<br>98.8 F. | Dissolved 12.5 mg Zeniquin in 15 cc Rebound and gave PO at 10:30 AM<br>Gave 12 mg Tamiflu/PO | Pinga is walking around house . . . slept in owner's bed . . . refused being given Rebound by syringe . . . comes when called . . . Physical exam is normal |
|---|---|---|

6th.

| Date:<br>Nov. 26, 2004<br>Temp:<br>100.6 F. | Gave 12 mg Tamiflu/PO at 5 PM | Urinated normal urine . . . passed 3 small firm BMs . . . jumped up to help iron clothes, vocal . . . First time temperature has been above 100 F. |
|---|---|---|

7th.

| Date:<br>Nov. 27, 2004<br>Temp:<br>98.8 F. | Dissolved 12.5 mg Zeniquin in 15 cc Rebound<br>Gave 12 mg Tamiflu/PO at 10:30 AM | Beginning 3rd day of Tamiflu . . . Pinga is more alert . . . began to eat Wellness dry cat food . . . had BM in litter box . . . continues to be given Rebound via syringe at home |
|---|---|---|

8th.

| Date:<br>Nov. 27, 2004<br>Temp:<br>Not Taken | Gave 12 mg Tamiflu/PO at 5 PM | Appears to be "normal", alert, active and interested in surroundings . . . Dispensed CNM-EN as a semi-soft food to try at home |
|---|---|---|

9th.

| Date:<br>Nov. 28, 2004<br>Temp:<br>100.1 F. | Dissolved 12.5 mg Zeniquin in 15 cc Rebound<br>Gave 12 mg Tamiflu/PO at 10:30 AM | Ate CMN-EN last night, urinated normally, almost "normal" . . . maybe weak in rear when playing with ball . . . shows interest when Jerry is tying shoe strings . . . this is a normal activity for Pinga |
|---|---|---|

10th.

| Date:<br>Nov. 28, 2004<br>Temp:<br>Not Taken | Gave 12 mg Tamiflu/PO at 5:30 PM | Pinga appears to be normal . . . this is his last treatment with Tamiflu. |
|---|---|---|

In Table 16, *E. coli*, a neuraminidase dependent bacteria, was cultured from Pinga's urine following an acute onset of vomiting and hematuria. She failed to respond to Zeniquin, but had a dramatic reversal when Tamiflu was started on Nov. 24, 2005 when she presented in an endotoxic condition. This case demonstrates the success of Tamiflu in cases of *E. coli* enterotoxemia.

The foregoing is merely illustrative of the invention and is not intended to limit the invention to the disclosed compounds. Variations and changes which are obvious to one skilled in the art are intended to be within the scope and nature of the invention which are defined in the appended claims.

What is claimed is:

1. A method for inhibiting neuraminidase dependent bacterial infections that are not viral generated dependent infections, wherein the neuraminidase dependent bacterial infections that are not viral generated dependent infections are selected from the group consisting of feline, canine, or raccoon parvoviral enteritis and canine kennel cough, from a disease-causing microorganism dependent on sialic acid metabolism, comprising administering to an animal in need thereof a therapeutically effective amount of a composition comprising one or more compounds, wherein one of the compounds comprises oseltamivir or zanamivir.

2. A method for treating neuraminidase dependent bacterial infections that are not viral generated dependent infections, wherein the neuraminidase dependent bacterial infections that are not viral generated dependent infections are selected from the group consisting of feline, canine, raccoon parvoviral enteritis and canine kennel cough, from a disease-causing microorganism dependent on sialic acid metabolism, comprising administering to an animal in need thereof a therapeutically effective amount of a composition comprising one or more compounds, wherein one of the compounds comprises oseltamivir or zanamivir.

3. A method for decreasing the probability of acquiring neuraminidase dependent bacterial infections that are not viral generated dependent infections, wherein the neuraminidase dependent bacterial infections that are not viral generated dependent infections are selected from the group consisting of feline, canine, or raccoon parvoviral enteritis and canine kennel cough, from a disease-causing microorganism dependent on sialic acid metabolism, comprising administering to an animal in need thereof a therapeutically effective amount of a composition comprising one or more compounds, wherein one of the compounds comprises oseltamivir or zanamivir.

4. A method of using an antiviral drug for human influenza, wherein the drug comprises oseltamivir or zanamivir, to treat neuraminidase dependent bacterial infections, that are not viral generated dependent infections, superinfections and coinfections which do not involve the human influenza virus A and/or B, wherein the infections to be treated are selected from the group consisting of feline, canine, or raccoon parvoviral enteritis and canine kennel cough, in clinical veterinary medicine, comprising administering to an animal in need thereof a therapeutically effective amount of a composition comprising one or more compounds, wherein one of the compounds comprises oseltamivir or zanamivir.

5. The method of claim 1, wherein oseltamivir or zanamivir is used to target neuraminidase dependent bacterial infections, superinfections, and coinfections, that are not dependent on viral neuraminidase, and that are selected from the group consisting of feline, canine, or raccoon parvoviral enteritis and canine kennel cough.

6. The method of claim 1, wherein the therapeutically effective amount of oseltamivir or zanamivir is from about 0.6 mg/lb to about 12 mg/lb.

7. The method of claim 1, wherein the therapeutically effective amount of oseltamivir or zanamivir is from about 0.3 mg/lb to about 10 mg/lb.

8. The method of claim 1, wherein the therapeutically effective amount of oseltamivir or zanamivir is from about 1 mg/lb.

9. The method of claim 2, wherein the therapeutically effective amount of oseltamivir or zanamivir is from about 0.6 mg/lb to about 12 mg/lb.

10. The method of claim 2, wherein the therapeutically effective amount of oseltamivir or zanamivir is from about 0.3 mg/lb to about 10 mg/lb.

11. The method of claim 2, wherein the therapeutically effective amount of oseltamivir or zanamivir is from about 1 mg/lb.

12. The method of claim 3, wherein the therapeutically effective amount of oseltamivir or zanamivir is from about 0.6 mg/lb to about 12 mg/lb.

13. The method of claim 3, wherein the therapeutically effective amount of oseltamivir or zanamivir is from about 0.3 mg/lb to about 10 mg/lb.

14. The method of claim 3, wherein the therapeutically effective amount of oseltamivir or zanamivir is from about 1 mg/lb.

15. The method of claim 1, wherein the oseltamivir or zanamivir is administered by any conventional route selected from the group consisting of oral, intravenous, intramuscular, intradermal, and subcutaneously.

16. The method of claim 2, wherein the oseltamivir or zanamivir is administered from about once a day to about 6 times a day.

17. The method of claim 2, wherein the oseltamivir or zanamivir is administered from about 10 doses over a period of 5 days to about 6 doses over a period of 3 days.

18. The method of claim 3, wherein the oseltamivir or zanamivir is administered from about once a day for 5 days.

* * * * *